US00PP08496P

United States Patent [19]

Meilland

[11] Patent Number: Plant 8,496

[45] Date of Patent: Dec. 14, 1993

[54] HYBRID TEA ROSE PLANT NAMED 'MEIRONSSE'

[75] Inventor: Alain A. Meilland, Antibes, France

[73] Assignee: The Conard-Pyle Company, West Grove, Pa.

[21] Appl. No.: 971,601

[22] Filed: Oct. 30, 1992

[51] Int. Cl.[5] ..... A01H 5/00

[52] U.S. Cl. ..... Plt./16

[58] Field of Search ..... Plt./11, 16, 17, 22, Plt./25

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly and continuously forms attractive double orange blossoms. The blossoms are Indian Orange and are edged with Capsicum Red. The buds assume a very elegant configuration. Such blossoms are long lasting and their cleaning ability is excellent. The plant exhibits a semi-erect growth habit, very vigorous vegetation, and is particularly well suited for growing in parks and gardens. Also, the new variety is not particularly affected by cryptogamic diseases.

1 Drawing Sheet

SUMMARY OF THE INVENTION

The new variety of Hybrid Tea rose plant was created by artificial pollination wherein two parents were crossed with previously had been studied in the hope that they would contribute the desired characteristics. The female parent (i.e., the seed parent) of the new variety was the Meigurami variety (non-patented in the United States) and the male parent (i.e., the pollen parent) was the product of the pollination of the Meinuzeten variety (U.S. Plant Pat. No. 4,224) by the Meinaregi variety (non-patented in the United States). The parentage of the new variety can be summarized as follows:

Meigurami × (Meinuzeten × Meinaregi).

The seeds resulting from the above pollination were sown and 39 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a continuous basis attractive long lasting double flowers which are Indian Orange and edged with Capsicum Red,
(b) exhibits a semi-erect growth habit,
(c) exhibits very vigorous vegetation,
(d) forms buds having a very elegant configuration, and
(e) is not particularly affected by cryptogamic diseases.

The cleaning ability of the blooms after flowering is excellent.

The new variety well meets the needs of the horticultural industry for a number of uses and is particularly well suited for growing as attractive ornamentation in parks and gardens.

The new variety has been found to undergo asexual propagation in France by a number of routes, including budding, grafting, cuttage, etc. The characteristics of the new variety have been found to be strictly transmissible by such asexual propagation from one generation to another.

The new variety has been named the Meironsse variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were three years of age and were observed during June while budded on *Rosa froebelii* understock and growing outdoors at LeCannet de Maures, Var, France.

DETAILED DESCRIPTION

Figures 1, 2, 3, 4, 5, 6, 7, 8, 9, 10, 11, 12, 13, 14:
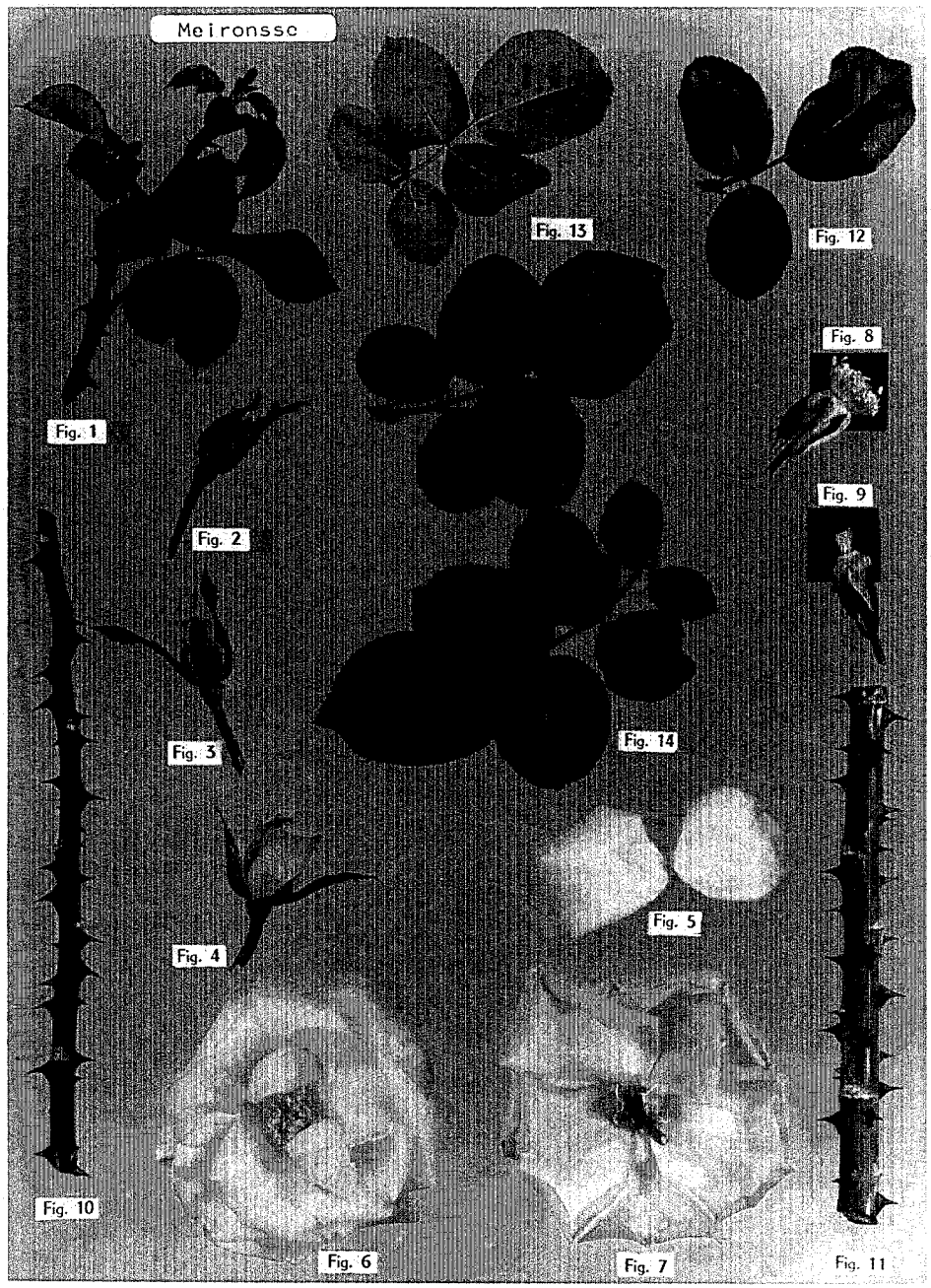
FIG. 1 illustrates a specimen of young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of two floral petals.
FIG. 6 illustrates a specimen of an open flower — plan view — obverse.
FIG. 7 illustrates a specimen of an open flower — plan view — reverse.
FIG. 8 illustrates a specimen of a floral receptacle showing the arrangement of the stamens and pistils.
FIG. 9 illustrates a specimen of a floral receptacle showing the arrangement of the pistils (stamens removed)
FIG. 10 illustrates a specimen of a flowering stem.
FIG. 11 illustrates a specimen of a main branch.
FIG. 12 illustrates a specimen of a leaf with three leaflets — plan view — upper surface.
FIG. 13 illustrates a specimen of two leaves with five leaflets — plan view — lower surface (top) and plan view — upper surface (bottom)
FIG. 14 illustrates a specimen of a leaf with seven leaflets — plan view — upper surface.

The chart used in the identification of the colors is that of The Royal Horticultural Society (R.H.S. Colour Chart). The description is based on the observation of three year old plants made during June while budded on *Rosa froebelii* understock and growing outdoors at Le-Cannet des Maures, Var, France. The coloration in common terms precedes reference to the chart.

Class: Hybrid Tea.

Plant:

*Height.*—Approximately 1.1 m.

*Habit.*—Semi-erect.

Branches:

*Color.*—Young stems: lettuce green, Yellow-Green Group 144A, and widely stained with reddish-brown coloration. Adult wood: bronze green, Yellow-Green Group 146A, and more or less suffused with reddish coloration.

*Thorns.*—Size: large. Quantity: as illustrated. Color: reddish on young stems and pinkish green changing to tan on adult wood.

Leaves:

*Stipules.*—Adnate, pectinate, very wide and linear.

*Petioles.*—Upper surface: striped reddish brown on young foliage and medium green on adult foliage with more or less glandular edges. Under surface: light green, and smooth.

*Leaflets.*—Number: 3, 5 (most often), and 7. Shape: generally rounded. Serration: single and regular. Texture: leathery. General appearance: ample, dense and bright foliage. Color (young foliage): Upper surface: lettuce green, Yellow-Green Group 144A, and stained with reddish-brown coloration. Under surface: lettuce green, Yellow-Green Group 144A, and stained with reddish-brown coloration. Color (adult foliage): Upper surface: dark green, Yellow-Green Group 147A. Under surface: light green, Green Group 137C.

Inflorescence:

*Number of flowers.*—1 to 3, usually a single bloom per stem.

*Peduncle.*—Straight and rigid, more or less stained with reddish coloration. The length is approximately 4 cm. on average.

*Sepals.*—Upper surface: tomentose, greenish, and more or less stained with reddish coloration. Under surface: medium green in coloration, the outer sepals have more or less appendiculated edges and terminate in a more or less developed leaf-like appendix.

*Buds.*—Shape: Oval. Length: approximately 2.5 to 3 cm. on average. Size: large. Color upon opening: Upper surface: Capsicum Red, Orange-Red Group 33A. Under surface: Capsicum Red, Orange-Red Group 33A, and widely suffused with Orange-Red Group 34A.

*Flower.*—Shape: cup-like and double. Diameter: approximately 12 to 13 cm. on average. Color (when opening begins): Upper surface: Capsicum Red, Orange-Red Group 33A. Under surface: Capsicum Red, Orange-Red Group 33A, and widely suffused with Orange-Red Group 34A. Color (when blooming): Upper surface: Indian Orange, Orange-Red Group 32B, and edged with Capsicum Red, Orange-Red Group 33A. Under surface: Shrimp Red, Orange-Red Group 33C. Color (at end of blooming): Upper surface: medium Rhodonite Red, Red Group 51B. Under surface: light Rhodonite Red, Red Group 51C. Fragrance: none. Lasting quality: very long. Petal number: approximately 25 to 27 on average. Texture: consistent. Petal drop: excellent. Petal configuration: rounded with reflective edges. Stamen number: approximately 133 on average. Anthers: normal ochre, located at the same level as the stigma. Filaments: orange red, and of irregular heights. Pistils: approximately 47 on average. Stigmas: normal, strawlike. Styles: strawlike and of irregular heights. Receptacle: smooth, medium green, more or less stained with reddish coloration, and in longitudinal section at the dehiscence of the anthers it is in the shape of a pitcher.

Development:

*Vegetation.*—Very vigorous.

*Blooming.*—Abundant and continuous.

*Aptitude to bear fruits.*—Good.

*Resistance to frost.*—Good.

*Resistance to diseases.*—Very good.

I claim:

1. A new and distinct variety of the Hybrid Tea rose plant characterized by the following combination of characteristics:

(a) forms in abundance on a continuous basis attractive long lasting double flowers which are Indian Orange and edged with Capsicum Red,
(b) exhibits semi-erect growth habit,
(c) exhibits very vigorous vegetation,
(d) forms buds having a very elegant configuration, and
(e) is not particularly affected by cryptogamic diseases;

substantially as herein shown and described.

* * * * *

Meironssc